United States Patent [19]

Chung

[11] Patent Number: 5,643,670
[45] Date of Patent: Jul. 1, 1997

[54] PARTICULATE CARBON COMPLEX

[75] Inventor: Deborah D. L. Chung, East Amherst, N.Y.

[73] Assignee: The Research Foundation of State University of New York at Buffalo, Buffalo, N.Y.

[21] Appl. No.: 99,863

[22] Filed: Jul. 29, 1993

[51] Int. Cl.⁶ .................................................. B32B 9/00
[52] U.S. Cl. .................. 428/367; 428/376; 428/418; 428/408; 428/398; 427/115; 427/122; 427/255.1; 427/376.6
[58] Field of Search ........................ 428/408, 367, 428/409, 376, 418, 398; 427/115, 122, 376.6, 249, 255.1, 216

[56] References Cited

U.S. PATENT DOCUMENTS

| | | | |
|---|---|---|---|
| 3,985,578 | 10/1976 | Witherspoon et al. | 429/44 |
| 4,565,684 | 1/1986 | Tibbetts et al. | |
| 4,663,230 | 5/1987 | Tennent | 428/367 |
| 4,786,568 | 11/1988 | Elmore et al. | 429/44 |
| 4,855,091 | 8/1989 | Genus et al. | 264/22 |
| 4,900,483 | 2/1990 | Witzke et al. | 264/29.2 |
| 4,929,514 | 5/1990 | Solomon et al. | 204/290 |
| 4,997,531 | 3/1991 | Yoshio et al. | |
| 5,082,595 | 1/1992 | Galckin | |
| 5,098,771 | 3/1992 | Friend | |
| 5,110,693 | 5/1992 | Friend et al. | |
| 5,124,075 | 6/1992 | Yasuda et al. | |
| 5,149,584 | 9/1992 | Baker et al. | |
| 5,165,909 | 11/1992 | Tennent | |
| 5,171,560 | 12/1992 | Tennent | |
| 5,304,326 | 4/1994 | Goto et al. | |
| 5,445,327 | 8/1995 | Creehan | |

OTHER PUBLICATIONS

Endo, et al., "Structural Improvement of Carbon Fibers Prepared From Benzene," *Japanese Journal of Applied Physics*, vol. 15, No. 11, pp. 2072–2076 (Nov. 1976).

Kato, et al., "Formation Of Vapor–Grown Carbon Fibers On A Substrate," *Carbon*, vol. 31, No. 7, pp. 989–994 (1992).

M. Egashira, et al., "Whiskerization of Carbon Beads by Vapor Phase Growth of Carbon Fibers to Obtain Sea Urchin–Type" *Carbon*, vol. 21, No. 1, pp. 89–92 (1983).

*Primary Examiner*—Merrick Dixon
*Attorney, Agent, or Firm*—Nixon, Hargrave, Devans & Doyle LLP

[57] ABSTRACT

The present invention relates to a particulate carbon complex made from a porous, particulate carbon substrate and a plurality of carbon filaments each having a first end attached to the porous, particulate carbon substrate and a second end distal from substrate. The complex is capable of transferring electrical current at a density of 350 to 10.000 mA/cm² for a $Fe^{+2}/Fe^{+3}$ oxidation/reduction electrochemical reaction couple carried out in an aqueous electrolyte solution containing 6 mM potassium ferrocyanide and 1M potassium nitrate. The complex is prepared by providing a porous, particulate carbon substrate with impregnated metal catalyst and contacting the substrate with a gaseous carbonaceous material under conditions effective to form a plurality of carbon filaments on the substrate. Generally, the complex includes particles of metal catalyst material at the end of the filaments distal from the substrate. The carbon complex is useful in electrochemical applications as well as in structural composites.

12 Claims, 8 Drawing Sheets

PARTICULATE CARBON COMPLEX

FIELD OF THE INVENTION

The present invention relates to a carbon complex and its process of manufacture.

BACKGROUND OF THE INVENTION

The superior mechanical and strength-to-weight properties of carbon fibers has led to an important class of high performance fiber/matrix composites. These high performance composites are particularly useful for the production of aircraft and automobile body parts for which both strength and light weight are critical. Such composites enable manufacturers to produce relatively light weight structures without sacrificing strength. Consequently, much research has been directed to producing carbon fiber materials with ever increasing high performance properties and physical features that make them more valuable in commercial products and processes.

Various processes have been developed over the years for the production of high performance carbon fiber materials. One of the leading processes for producing high performance carbon fibers is the so-called PAN process wherein polyacrylonitrile is used as a precursor fiber. The PAN process typically starts with a highly prestretched PAN fiber and involves three steps. First is a stabilization treatment wherein the PAN fiber is heat treated in air at a temperature from about 200° to 300° C. for one or more hours. In the second step, the fiber is carbonized at a temperature above about 1100° C. in a non-oxidizing atmosphere. Last is a post heat treatment at temperatures up to about 2500° C. to graphitize the fiber and give it high performance properties. It is in this post heat treatment step that the chemical composition, the crystalline structure, and the mechanical properties are strongly influenced.

There has been an intense effort to develop methods of spinning and carbonizing hydrocarbon pitch fiber to reduce precursor filament cost and weight loss. However, such processes require pitch pretreatment, spinning conditions, and post-treatments to insure correct orientation of carbon atoms in the final products. As a result, use of spun and carbonized hydrocarbon pitch has been nearly as expensive as using the previously noted methods involving organic polymers. Both methods require use of continuous filaments to achieve high orientation and good properties. There is a practical fiber diameter lower limit of 6 to 8 micrometers. Thinner fibers break during spinning and require excessive post-treatment.

An entirely different approach for carbon fiber formation involves the preparation of carbon filaments through the catalytic decomposition at metal surfaces of a variety of carbon containing gases, e.g., $CO/H_2$, hydrocarbons, and acetone. These filaments are found in a wide variety of morphologies (e.g., straight, twisted, helical, branched) and diameters (e.g., ranging from tens of angstroms to tens of microns). Usually, a mixture of filament morphologies is obtained, frequently admixed with other, non-filamentous carbon (cf. Baker and Harris, *Chemistry and Physics of Carbon*, Vol. 14, 1978). Frequently, the originally-formed carbon filaments are coated with poorly organized thermal carbon.

The vapor decomposition technique for forming carbon filaments has been extensively studied. U.S. Pat. No. 4,855,091 to Geus prepares carbon filaments by exposing a thermostable substrate covered with reduced metal particles to a carbon-containing gas at 200° to 700° C. U.S. Pat. No. 5,149,584 to Baker et al. deposits a catalyst comprising a group IB element and a second metal which is either iron, nickel, cobalt, or zinc on a carbon fiber substrate and contacts it with carbonaceous material at 500° to 700° C. U.S. Pat. No. 4,565,684 to Tibbetts et al. discloses growing graphite fibers on a suitably nucleated ceramic surface by passing methane gas over the substrate at elevated temperatures, and thickening the initially-formed microscopic carbon filaments by increasing the concentration of methane. Endo et al., "Structural Improvement Of Carbon Fibers Prepared From Benzene," *Japanese Journal of Applied Physics*, Vol. 15, No. 11, pp. 2073–76 (November, 1976) discloses the preparation of carbon fibers by thermal decomposition of benzene at 1050° to 1080° C. Kato et al., "Formation Of Vapor-Grown Carbon Fibers On A Substrate," *Carbon*, Vol. 31, No. 7, pp. 989–94 (1992) relates to growing fibers on activated carbon pellets by impregnating the pellets with an iron catalyst and introducing hydrogen sulfide and benzene in a gaseous state with "[n]o carbon fibers ... produced without the feed of sulfur". U.S. Pat. Nos. 4,663,230, 5,165,909, and 5,171,560 to Tennent disclose the formation of substantially cylindrical carbon fibrils with an outer region of multiple layers of ordered carbon atoms and a distinct inner core region by contacting a metal particle (preferably supported on a refractory material) with a gaseous carbon-containing compound. M. Egashira et al., "Whiskerization of Carbon Beads by Vapor Phase Growth of Carbon Fibers to Obtain Sea Urchin-Type Particles," *Carbon*, vol. 21, no. 1., pp. 89–92 (1983) produces carbon filaments on hard, non-porous, sulfur-containing carbon beads.

In many cases, these vapor decomposition processes form filaments which can be utilized in high strength applications. There is also some mention that such filaments can be utilized as an electrical conductor or in electrochemical applications, such as for electrodes. See U.S. Pat. No. 4,855,091 to Geus et al. and U.S. Pat. Nos. 4,663,230, 5,165,909, and 5,171,560 to Tennent et al. Unfortunately, the art has been unable to produce carbon filament materials which are commercially useful in such electrical applications. This is due to the low electron transfer rates for such materials. The need, therefore, remains for vapor decomposition products which can be effectively utilized in electrical and electrochemical applications.

SUMMARY OF THE INVENTION

The present invention relates to a particulate carbon complex having a porous, particulate carbon substrate and a plurality of carbon filaments each with a first end attached to the substrate and a second end distal from the substrate. The particulate carbon complex is capable of transferring electrical current at a density of 350 to 10,000 $mA/cm^2$ for a $Fe^{+2}/Fe^{+3}$ oxidation/reduction electrochemical reaction couple carried out in an aqueous electrolyte solution containing 6 mM potassium ferrocyanide and 1M potassium nitrate. The complex will usually further include a particulate metal catalyst material at the second end of each carbon filament selected from the group consisting of iron, nickel, cobalt, zinc, platinum, and mixtures thereof. The particulate substrate desirably has pores less than 5000 Angstroms, while the particulate metal catalyst is similarly sized.

The carbon complex of the present invention is prepared by providing a porous, particulate carbon substrate impregnated with a metal catalyst material. The impregnated substrate is then contacted with a gaseous carbonaceous material under conditions effective to form the particulate carbon complex.

The carbon complex of the present invention is particularly useful in conjunction with electrochemical devices. Such devices include an electrode formed from the carbon complex having a porous particulate carbon substrate and a plurality of carbon filaments each having a first end attached to the substrate and a second end distal from the substrate.

The complex of the present invention is also useful as a composite in admixture with a dissimilar material. Suitable dissimilar materials include metals, polymers, glasses, ceramics, and mixture thereof.

DETAILED DESCRIPTION OF THE INVENTION

Figure 1A:
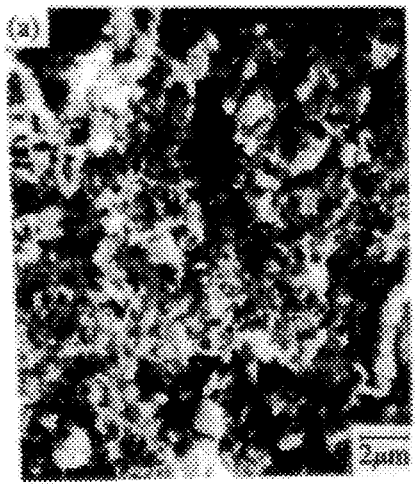
FIG. 1A is a scanning electron micrograph showing the morphology of an iron catalyst on acetylene carbon black.

The present invention relates to a particulate carbon complex which includes a porous particulate carbon substrate and a plurality of carbon filaments each having a first end attached to the substrate and a second end distal from the substrate. The particulate carbon complex is capable of transferring electrical current at a high charge density.

In large part, the substrate utilized in prior art vapor decomposition processes are merely surfaces to grow carbon filaments on. Once filament growth is completed, the filaments are harvested and the substrate disposed of. As a result, conductive and non-conductive materials (e.g., refractory supports like alumina, carbon, quartz, or silicate) have been disclosed as useful even where electrical applications are suggested for filament production. See U.S. Pat. Nos. 4,663,230, 5,165,909, and 5,171,560 to Tennent et al. Even where a carbon substrate (e.g., carbon fibers) are suggested in the prior art, the complex of that substrate with a plurality of filaments extending from it have insufficient electron transfer rates to function satisfactorily in electrochemical applications. Such smooth carbon substrates lack the porosity and pore size needed to make the complex suitable for such uses.

Applicant has found that, in order for the carbon complex of the present invention to be useful in electrochemical applications, the substrate must be a porous carbonaceous material, preferably with pores less than 5000 Angstroms in diameter. A particularly preferred porous carbon substrate is carbon black, such as acetylene carbon black. Another carbonaceous material with a porosity and pore size suitable for forming carbon complexes useful in electrochemical applications is activated carbon. With such materials, the carbon complex of the present invention is capable of transferring current at a high charge density of 350 to 10,000 mA/cm$^2$, preferably 2000 to 9000 mA/cm$^2$, most preferably 7000 to 8000 mA/cm$^2$, for a $Fe^{+2}/Fe^{+3}$ oxidation/reduction electrochemical reaction couple carried out in an aqueous electrolyte solution containing 6 mM potassium ferrocyanide and 1M potassium nitrate. The $Fe^{+2}/Fe^{+3}$ oxidation/reduction electrochemical couple is a well known couple used to test the electrochemical behavior of materials. It refers to a pair of oxidation and reduction reactions. The oxidation reaction is $Fe^{+2}+e^- \rightarrow Fe^{+3}$, while the reduction reaction is $Fe^{+3} \rightarrow Fe^{+2}+e^-$. Use of this test system is not intended to limit the scope of the present invention; it is simply the standard used to define the electrochemical current density of the carbon complex of the present invention as well as that of other test materials.

It is also believed that the use of substrates with pores having diameters below 5000 Angstroms enhances the adhesion of filaments to the substrate compared to substrates with larger pores.

The plurality of filaments each have a diameter of less than 5000 Angstroms, preferably 0.05 to 0.2 μm. The carbon filaments can range in length from very short nodules (having an aspect ratio of as low as 1) to very long strands (having aspect ratios approaching infinity). Generally, however, their length is at least five times their diameter.

The carbon filaments each comprise a hollow core surrounded by a substantially continuous layer of carbon. The carbon layer preferably comprises layers of ordered carbon atoms oriented in a curved configuration, like a fish rib bone (i.e. graphitic domains having their c-axis at an oblique angle to the cylindrical axis of the filament and are in crystalline form).

It is contemplated that a wide variety of transition metals, in particulate form, can be utilized as catalysts to form the carbon complex of the present invention. In its final form, the carbon complex will usually be utilized with the particulate catalyst material on the ends of the filaments distal from the substrate. However, such catalyst materials can be removed from the complex by selective chemical etching. Suitable particulate metal catalyst materials are formed from metals, like iron, nickel, cobalt, zinc, platinum, and mixtures thereof. These catalyst materials do not need to be activated with sulfur, as in Kato et al., "Formation Of Vapor-Grown Carbon Fibers On A Substrate," *Carbon*, Vol. 30, No. 7, pp. 989-94 (1992), in order to produce carbon filaments. In the carbon complex of the present invention, the metal catalyst material is at the ends of the filaments distal from the substrate, because, as the filaments grow, the particles of metal catalyst material are lifted off the substrate by the filaments. A minor amount of metal catalyst material, which has not catalyzed carbon filament formation remains on the surface of the particulate carbon substrate. The presence of such unutilized catalyst is minimized when the metal particles are sufficiently small to fit into the pores of the carbon substrate. Generally, particles having a diameter below 5000 Angstroms, preferably below 1000 Angstroms, are suitable.

In the process of the present invention, any number of well known procedures can be utilized to impregnate the porous carbon substrate with metal catalyst material. One procedure involves impregnating the porous particulate carbon substrate with a metal salt solution and drying the impregnated material at a low temperature (such as 70° C.) in a vacuum in order to prevent oxidation of the catalyst. Suitable metal salts include carbonates, bicarbonates, nitrates, citrates, and oxalates of the above-described metal catalyst materials. The salts can be hydrated (e.g., $Fe(NO_3)_3 \cdot 9H_2O$).

To produce the carbon complex of the present invention, the porous carbon substrate impregnated with metal catalyst material is contacted with gaseous carbonaceous material under conditions effective to form a plurality of carbon filaments each having a first end attached to the substrate. While not wishing to be bound by theory, it is believed that the gaseous carbonaceous material reacts with the catalyst material to form an active catalyst phase, probably a metal carbide. Generally, such contact is at a temperature of 500° to 1200° C., for a time period of 10 minutes to 8 hours, and at a pressure of 0.1 to 10 atmospheres. In this process, the gaseous carbonaceous material is mixed with an inert, non-carbonaceous carrier gas (e.g., nitrogen). The gaseous carbonaceous material is contacted with the substrate such that the flow rate ratio of the carbonaceous gas to the carrier gas ranges from 10:100 to 25:100. At a ratio of more than 25:100, the catalyst tends to be "poisoned" due to carbon deposition on it. Once the catalyst is poisoned, filament growth stops.

It is contemplated that a variety of carbon-containing compounds are suitable as the gaseous carbonaceous material of the present invention. Suitable materials include carbon monoxide, saturated aliphatic hydrocarbons, olefinic hydrocarbons, aromatics, oxygen-containing organics, and mixtures thereof. Suitable aromatic include benzene, toluene, xylene, cumene, ethylbenzene, naphthalene, phenanthrene, anthracene, or mixtures thereof. Methane, ethane, propane, and mixtures thereof are useful saturated aliphatic hydrocarbons, while suitable olefinic hydrocarbons include ethylene, propylene, acetylene, or mixtures thereof. Useful hydrocarbons containing oxygen include, e.g., alcohols such as methanol or ethanol, ketones such as acetone, and aldehydes such as formaldehyde or acetaldehyde or mixtures thereof. Methane is preferred due to its availability, thermal stability, and lack of toxicity.

In some cases, it may be desirable to impart porosity to the filaments after forming the carbon complex of the present invention. This can be achieved by subjecting the complex to an activation step. Any conventional procedure used to activate carbon can be employed. Such procedures involve an oxidation treatment, such as thermal, chemical, electrochemical, or electromagnetic radiation oxidation. A particularly preferred activation technique involves heating the carbon complex and subjecting the plurality of carbon filaments to partial oxidation with a sub-stoichiometric amount of air or oxygen.

An important use of the carbon complex of the present invention is in electrochemical applications. It is particularly useful in forming electrodes for batteries, biomedical sensing devices, pH meters, chemical analytical equipment, and electrical conductors. Such electrodes can be formed purely from the carbon complex of the present invention which has been compacted into the shape of an electrode. No binders, which are potentially incompatible with certain electrolytes, are necessary. Electrodes, can also be formed from blends of the carbon complex of the present invention with carbonaceous materials conventionally used in electrodes. Alternatively, the carbon complex of the present invention can be blended as a composite with other materials conventionally utilized in electrodes which are either non-conductive or have low conductivity. For example, the carbon complex of the present invention can be mixed with manganese dioxide ($MnO_2$) or carbon monofluoride ($CF_x$) to form battery electrodes.

Manganese dioxide ($MnO_2$), for example, is known to be a good cathode material for aqueous batteries and has recently been commercialized for cathode use in lithium batteries. $MnO_2$ can be either chemically or electrolytically produced. The physical, chemical, and electrical properties of $MnO_2$ are dependent upon its manufacturing process. Electrolytic production results in good porosity and high depolarizing characteristics, while chemically produced $MnO_2$ has a high activity. During discharge, $MnO_2$ is reduced from the tetravalent to the trivalent species. Performance is dependent upon the crystalline state, the level of hydration, and the activity of the $MnO_2$. Both aqueous and organic electrolytes can be used with $MnO_2$ cathodes. The aqueous electrolyte/$MnO_2$ cell, in existence for more than 100 years, commonly utilizes a zinc anode while organic electrolyte/$MnO_2$ cells, only recently developed (since 1970), are constructed with lithium anodes. Two primary aqueous electrolyte/$MnO_2$ cells have dominated the market, the zinc-carbon or Leclanche cell and, with increasing popularity since 1940, the alkaline zinc/$MnO_2$ cell. The increased popularity of the alkaline zinc/$MnO_2$ cell is due to its superior performance at high current drains, continuous discharge, and low temperatures as well as its better shelf life over the Leclanche cell under the same operating conditions. Energy densities of around 100 W-h/kg are typically achieved. Lithium (Li) anode cells are gradually replacing these conventional battery systems because they offer still improved energy densities and operate over a wider temperature range while maintaining shelf life. The Li/$MnO_2$ cells achieve energy densities of just over 200 W-h/kg.

Carbon monofluoride ($CF_x$) is another cathode material used in high energy density, high voltage batteries. It is an intercalation compound which, while being electrochemically active, is chemically stable in organic electrolytes and does not thermally decompose at temperatures up to 400° C. The end result is a battery with an even wider temperature range and longer storage life capability. $CF_x$ is a nonconductive material which produces conductive carbon during discharge. As discharge progresses, the cell's conductivity increases which improves the regulation of the cell discharge voltage and increases discharge efficiency. Lithium fluoride, the discharge product, precipitates in the cathode structure. Energy densities up to 300 W-h/kg have been obtained from Li/$CF_x$ cells.

The carbon complex of the present invention can also be utilized to form composites with other dissimilar materials.

Suitable dissimilar materials include metals, ceramics, glasses, polymers, and mixtures thereof. Such composites are prepared by blending the particulate carbon complex of the present invention with these dissimilar materials in solid particulate form or in liquid form. When utilizing a solid blending technique, the carbon complex of the present invention is advantageous, because it is in a particulate form and can be much more easily dispersed than conventional carbon fibers or carbon filaments harvested from substrates in prior processes.

A variety of polymers can be utilized to form composites with the carbon complex of the present invention. Such polymers include, for example, polyamides, polyesters, polyethers, polyphenylenes, polysulfones, polyurethanes, or epoxy resins. Preferred embodiments include elastomers, thermoplastics, and thermosets.

In another embodiment, the composite contains an inorganic material, e.g., a ceramic material or a glass. Preferred embodiments include plate glass and other molded glass, silicate ceramics, and other refractory ceramics such as aluminum oxide, silicon carbide, silicon nitride, and boron nitride.

In still another embodiment, the composite includes a metal. Suitable metals include aluminum, magnesium, lead, zinc, copper, tungsten, titanium, niobium, hafnium, vanadium, and alloys thereof.

Due to the present carbon complex's ability to transfer electrons at a high density, smaller quantities of it can be utilized (compared to conventional forms of carbon) to deliver a given quantity of power. As a result, the size of electrodes, and therefore, the battery can be reduced. Alternatively, the electrode and battery sizes can be maintained to produce a battery with more power than a battery of the same size with a conventional carbon electrode. The carbon complex of the present invention is advantageously utilized in battery applications, because, compared to similar substrates without filaments, such complexes have a higher capacity per unit density at at least certain electrode densities.

The carbon complex of the present invention can also be advantageously utilized in mechanical applications to improve thermal and electrical conductivity, to retard crack propagation by providing multiple channels for crack growth, and to decrease the coefficient of thermal expansion of composites containing the carbon complex of the present invention. In addition, the complex's improved thermal and electrical conductivity can be useful in electrical applications.

EXAMPLES

Example 1

Catalyst Preparation

Ferric nitrate was selected as the catalyst in the process. The ferric nitrate ($Fe(NO_3)_3 \cdot 9H_2O$) was first dissolved in methanol to form a 20% (by weight) solution. Then the substrate (i.e., acetylene carbon black (Grade AB50P from Chevron Chemical Company)) was mixed with the solution and dried in a vacuum furnace at 60° to 70° C. overnight. The catalyst loading for different substrates corresponds to a ferric nitrate:substrate ratio of 1:1 to 5:1 in weight.

Apparatus

A three-zone furnace made by Lindberg, Watertown, Wisconsin was used. It was programmable to give a constant temperature. The growth reactor was a quartz tube with a 2 inch inner diameter.

Process

A layer of substrate was placed in an alumina boat. The reactor was first purged with $N_2$ for about 1 hour to eliminate oxygen in the reactor. Then, the temperature was raised to 500° C., at which hydrogen was introduced in order to reduce the catalyst. After 2 hours, the $H_2$ flow was ceased and the temperature was raised to 670° C. Acetylene gas was introduced when the reactor reached 670° C. The furnace was held at 670° C. for 5 hours.

Results

Figure 1B:
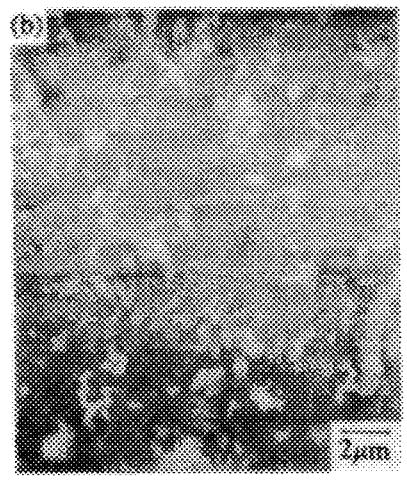
FIG. 1B is a scanning electron micrograph showing the back scattering of the image of FIG. 1A.
Figure 1C:
FIG. 1C is a scanning electron micrograph showing the carbon complex of the present invention with carbon filaments grown on acetylene carbon black, using ferric nitrate as the catalyst.

FIG. 1A shows the morphology of the iron catalyst on the surface of acetylene carbon black. The catalyst particles had an irregular shape, and their size ranged from 1 to 2 µm. FIG. 1B is the back-scattered electron image of FIG. 1A, showing the catalyst particles as bright regions. FIG. 1C shows the result of filament growth. A mixture of entangled filaments (about 1 µm in diameter) and carbon nodules (0.1 to 1 µm in size) were obtained. However, the proportion of nodules was lower than when graphite flakes were used as the substrate. The graphite filaments can provide good electrical conductivity, while carbon nodules provide a higher surface area. The presence of both is ideal for the electrode application.

Since acetylene black is a porous material, the catalyst solution was absorbed into the interconnected micropores of the acetylene black by capillary action. During drying, the outer surface of the acetylene black dried first. Then, the catalyst solution inside the acetylene black diffused outward and deposited catalyst particles in the surface region of the acetylene black. The porous nature of the acetylene black confined the catalyst particles and prevented them from coagulation. This process resulted in fine catalyst particles. Their size may depend on the size of the micropores and the concentration of the catalyst solution. Since the pore size of the acetylene black was mostly ten to several hundred Angstroms, the catalyst particle size was also mostly in that range. This particle size range is suitable for catalytic growth of carbon filaments. Therefore, it is easier to grow filaments on acetylene black than on graphite flakes, carbon fibers, or glassy carbon, which are much less porous. The large catalyst particles, though relatively few, were inactive in the catalyzed growth of carbon filaments. Instead, carbon deposited from the vapor phase and formed carbon filaments on the acetylene carbon black.

Example 2

Figure 2A:
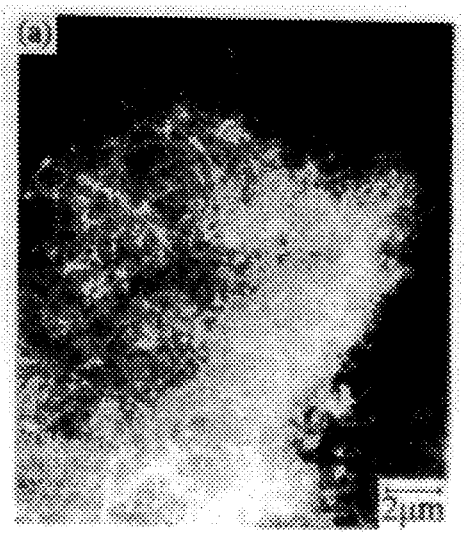
FIG. 2A is a scanning electron micrograph showing the carbon complex of the present invention with carbon filaments grown on acetylene carbon black, using nickel nitrate as the catalyst.
Figure 2B:
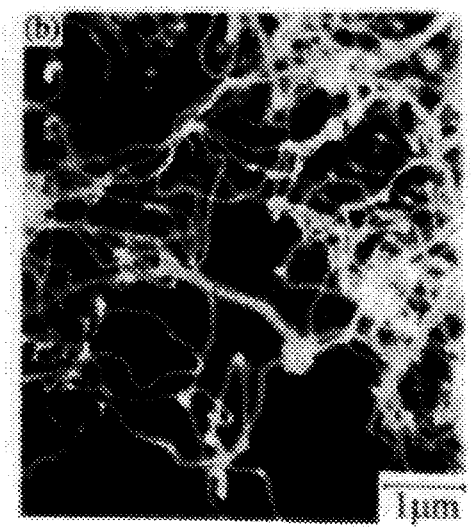
FIG. 2B is a scanning electron micrograph showing the carbon complex of FIG. 2A at a higher magnification.

Carbon complexes were prepared as in Example 1, except that (i) nickel nitrate instead of ferric nitrate was used as the catalyst, (ii) no hydrogen was used, so that the 500° C. heating step was eliminated, (iii) the furnace was held at 670° C. for 30 min, and (iv) graphite powder, carbon black, and carbon fibers were used as substrates. In other words, the process involved (i) purging the reactor containing one of the substrates with $N_2$ at a flow rate of 100 cc/min, (ii) raising the temperature to 670° C., (iii) introducing acetylene gas at a flow rate of 20 cc/min while maintaining the $N_2$ low, (iv) after 30 min at 670° C. in the presence of acetylene, stopping the acetylene gas flow and allowing the reactor temperature to fall, and (v) stopping the $N_2$ flow when the reactor had cooled to room temperature. This process was repeated for each of the different substrates. FIG. 2A is a scanning electron microscope photograph showing the resulting carbon complex with carbon black as the substrate. FIG. 2B also shows this complex but at a higher magnification than FIG. 2A.

Example 3

The electrochemical behavior of the carbon complexes prepared in Example 2 were compared. The study was carried out using cyclic voltammetry (CV). A Bioanalytical Systems CV cell was used in conjunction with the Headstart Electrochemistry program (developed by EG&G Princeton Applied Research), a potentiostat, and an IBM personal computer. A saturated calomel electrode served as reference with a platinum wire used as the auxiliary electrode. The working electrode was a holder typically used for carbon paste electrodes. The carbon complex was used to fill the cavity in the same manner as carbon paste, but without the conventional paraffin oil binder. Testing was conducted in 6 mM potassium ferrocyanide ($K_3Fe(CN)_6$) as the electroactive species and in 1M potassium nitrate ($KNO_3$) in water as the supporting electrolyte. This solution allowed study of the $Fe^{+2}/Fe^{+3}$ oxidation/reduction couple.

Figure 3A:
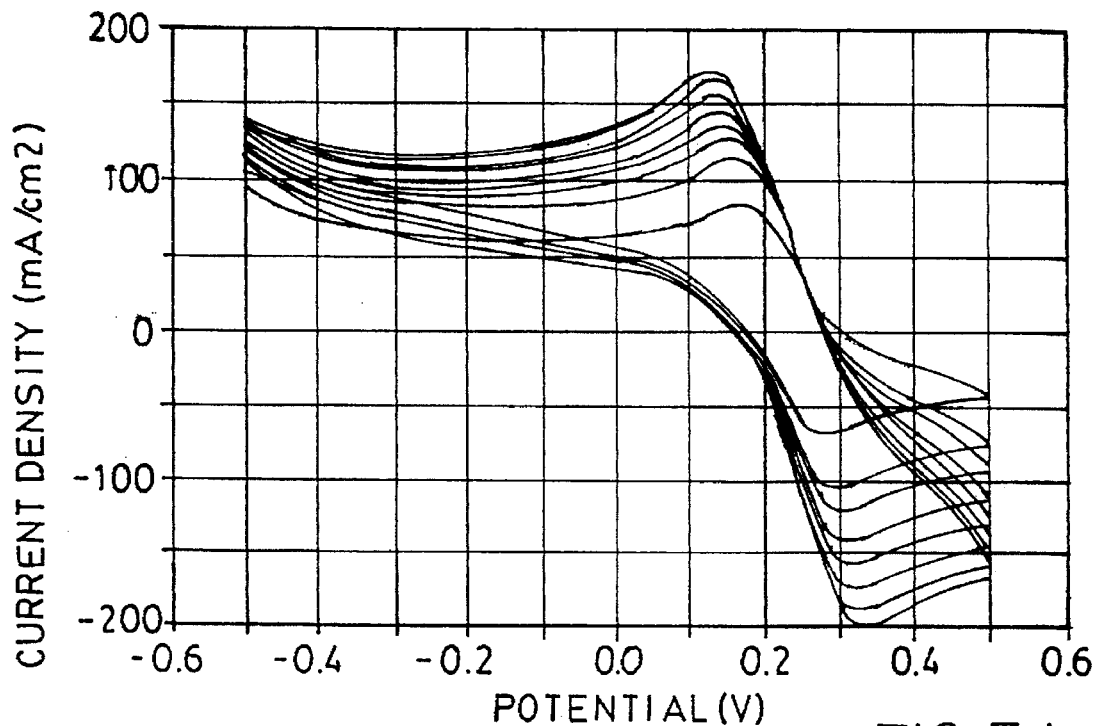
FIG. 3A is a voltammetric response plot of current density versus potential for the carbon complex of the present invention with a graphite substrate.
Figure 3B:
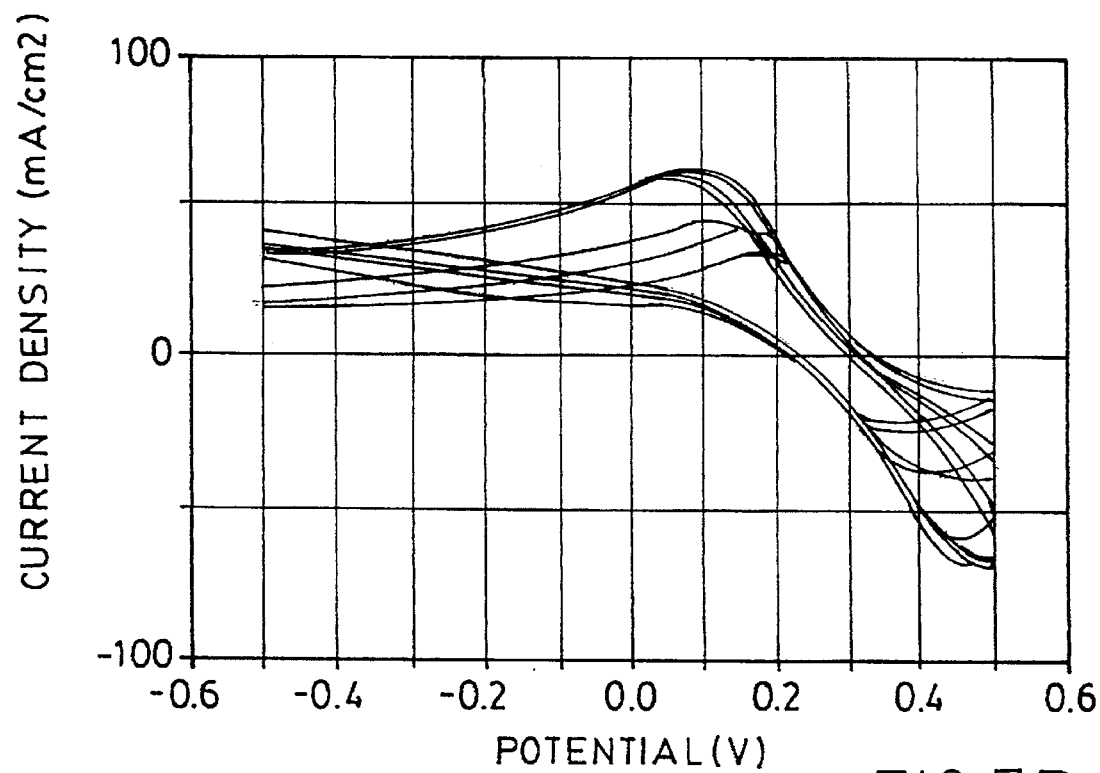
FIG. 3B is a voltammetric response plot of current density versus potential for plain graphite.

The voltammetric responses for the complex made from plain graphite powder (FIG. 3A versus FIG. 3B, respectively) the complex made from carbon black versus plain carbon black (FIG. 4A versus FIG. 4B, respectively), and the complex made from carbon fibers versus plain carbon fibers (FIG. 5A versus FIG. 5B, respectively) were all evaluated.

As shown in these figures, the presence of filaments dramatically improves the electrochemical performance of the plain substrate. This is demonstrated by the increase in electron transfer rate and enhanced reversibility of the redox reactions of the carbon complexes of carbon substrates with a plurality of filaments. This improvement is attributed to increased surface area and particulate connectivity which translates into improved conductivity.

Figure 4A:
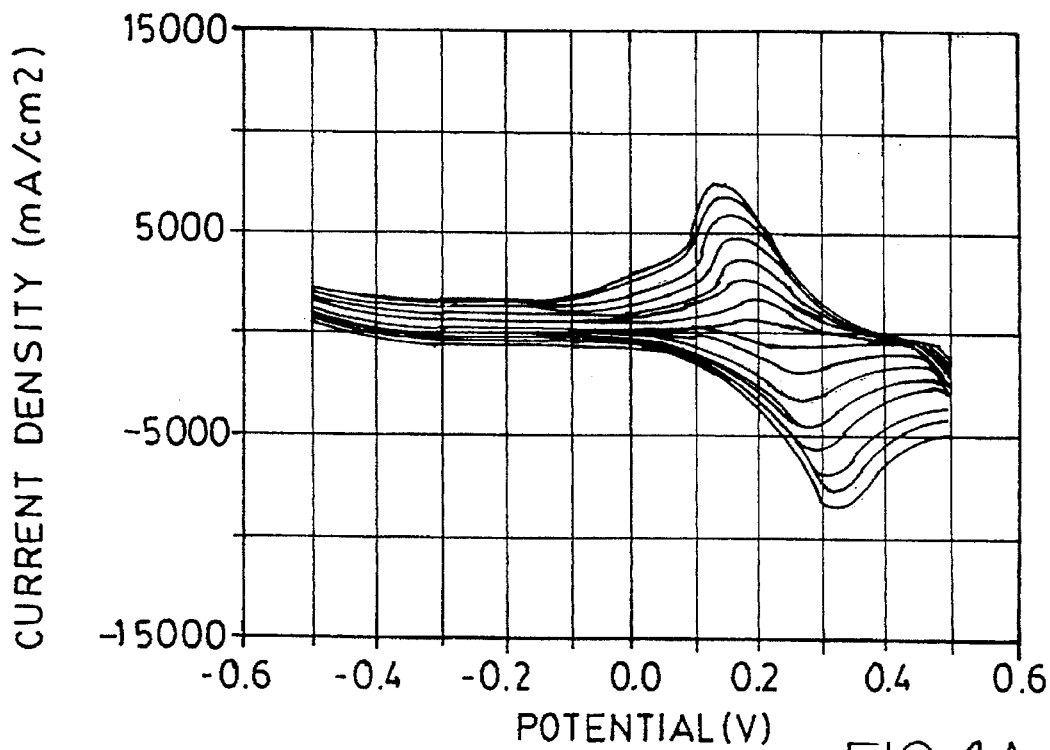
FIG. 4A is a voltammetric response plot of current density versus potential for the carbon complex of the present invention with a carbon black substrate.
Figure 4B:
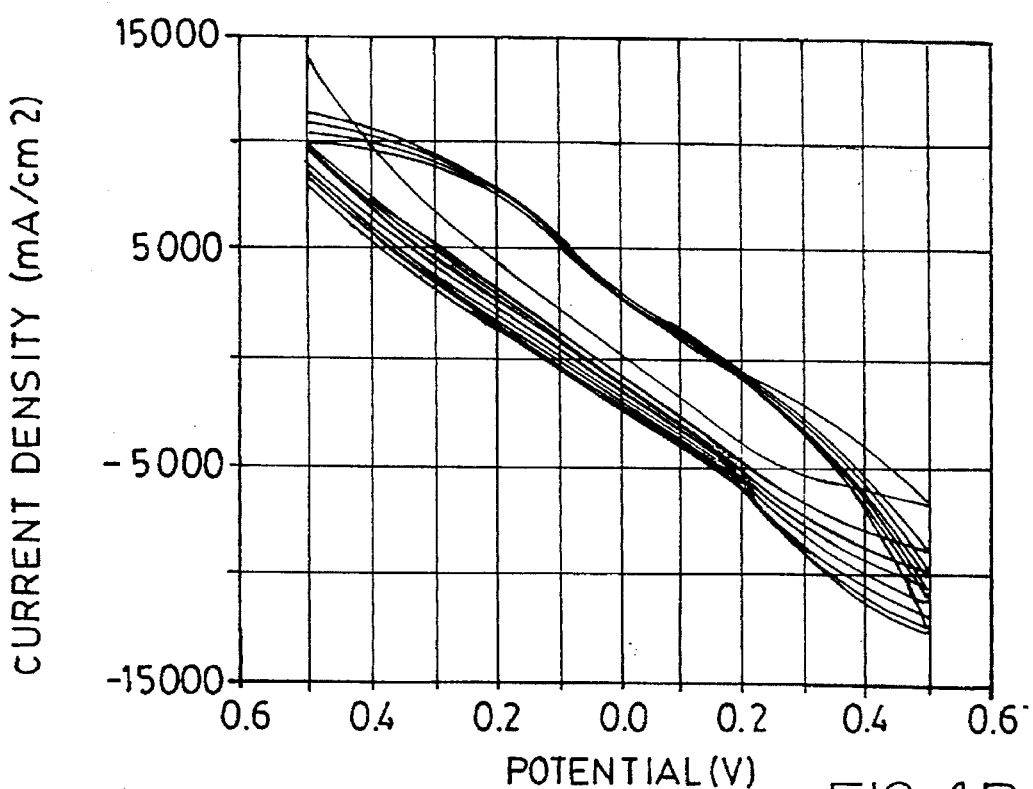
FIG. 4B is a voltammetric response plot of current density versus potential for plain carbon black.
Figure 5A:
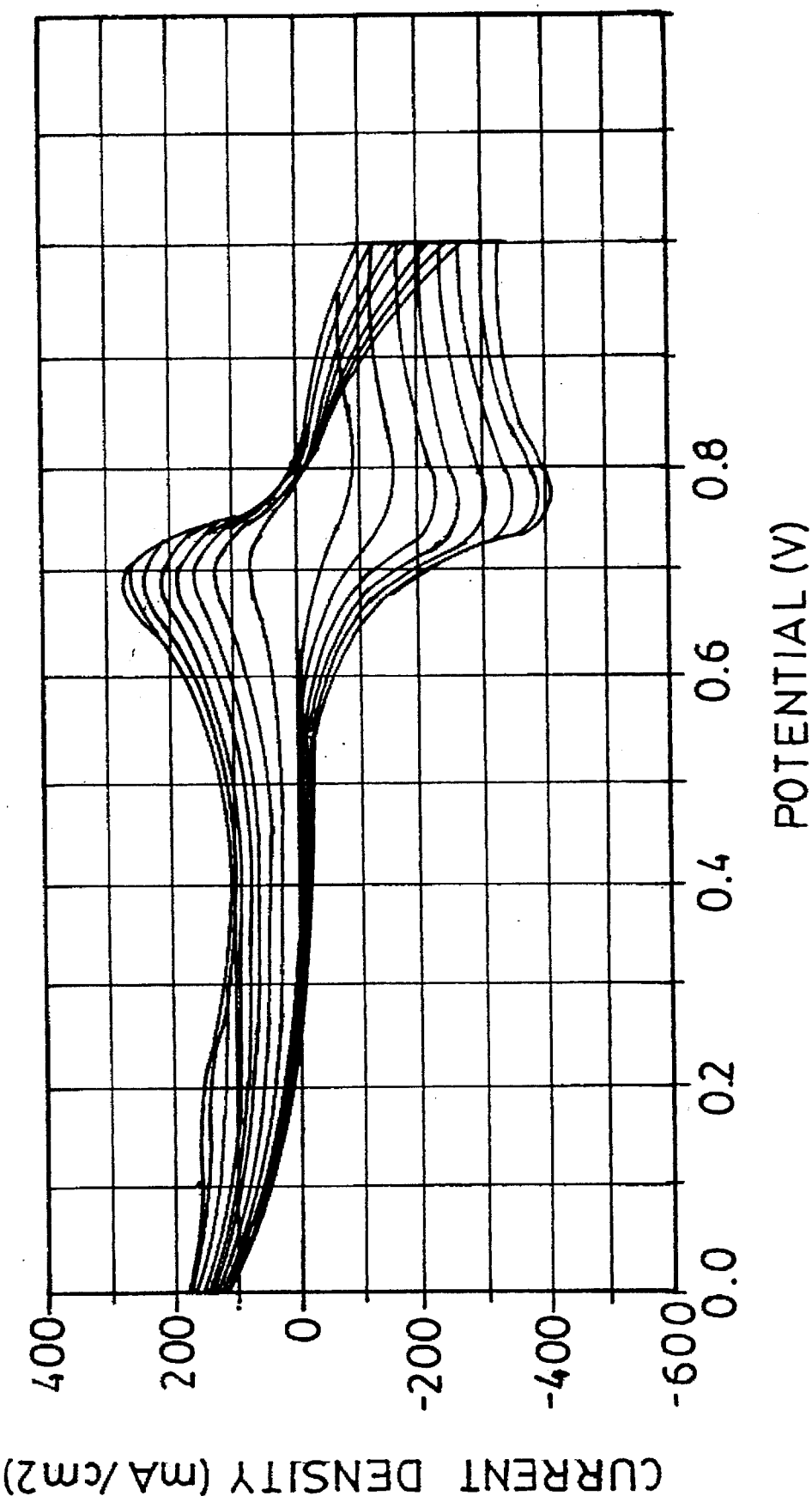
FIG. 5A is a voltammetric response plot of current density versus potential for the carbon complex of the present invention with a carbon fiber substrate.
Figure 5B:
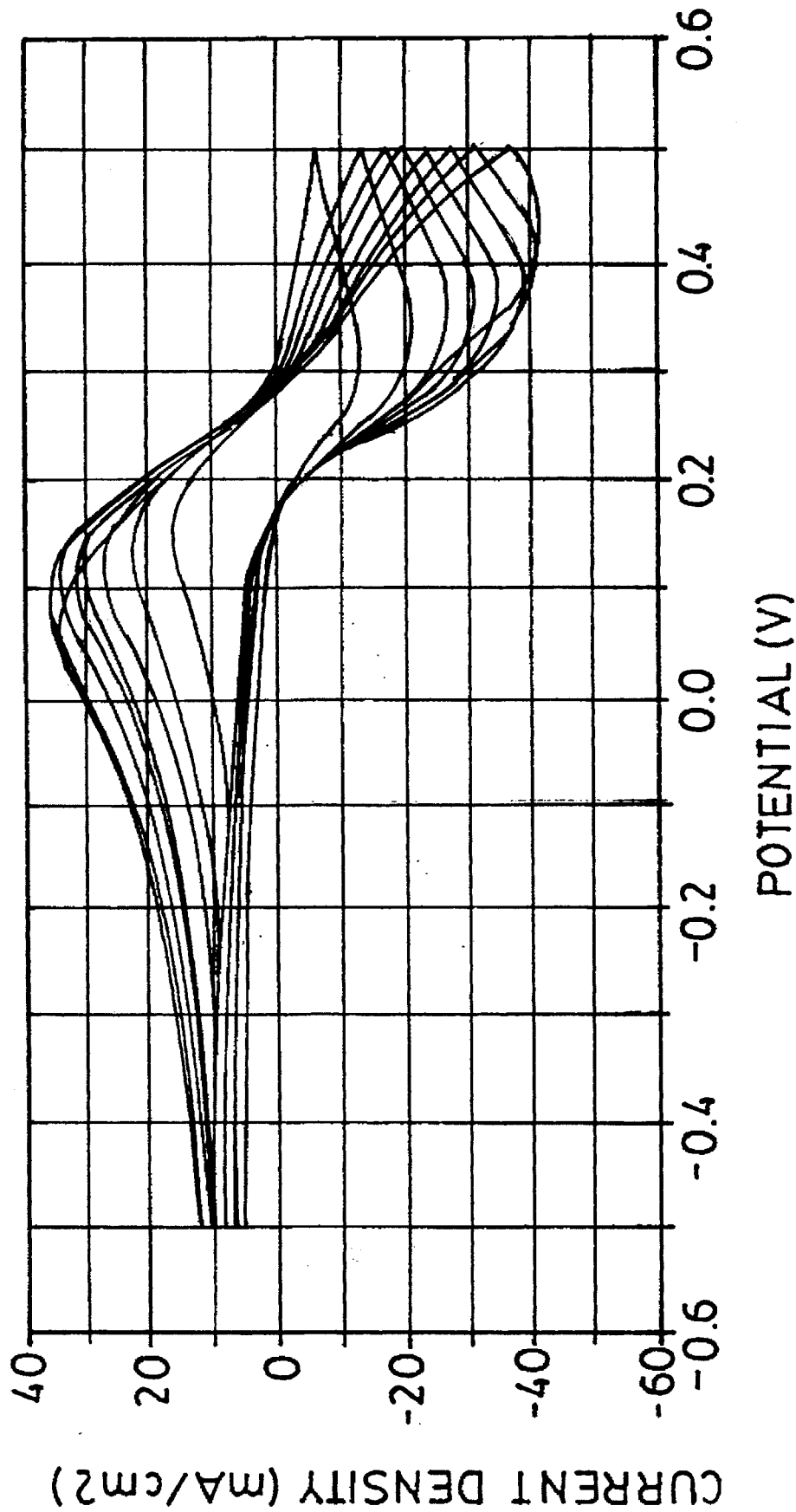
FIG. 5B is a voltammetric response plot of current density versus potential for the plain carbon fibers.

Particularly noteworthy is the high voltammetric response achieved with carbon complexes using carbon black as the substrate compared to that achieved with complexes made from other carbon substrates. More particularly, FIG. 4A shows that a complex with a carbon black substrate has a peak current density of about 7500 mA/cm$^2$. Even platinum, commonly used in research and considered an ideal electrode, only achieves a peak current density of about 1,700 mA/cm$^2$. Furthermore, graphite powder and carbon fibers only achieve peak current densities of 175 mA/cm$^2$ (FIG. 3B) and 300 mA/cm$^2$ (FIG. 5B), respectively. This over 20-fold increase in electron transport capability for such complexes formed from the microporous carbon black substrate imparts dramatic advantages. In batteries, electrodes made from such complexes can decrease size and/or increase power.

Example 4

To assess discharge capability, constant current plate-to-plate discharge testing was conducted. A cut-down AA battery case was used as the positive electrode current collector. The carbon was placed inside the case and separated from the lithium by a nonconductive glass fiber paper. Insulative polymer disks were placed on top of the assembly and held in place with a metal clip. The assembly was immersed in a bromine chloride complex electrolyte. The discharge mechanism comprised reduction of complexed thionyl chloride at the carbon electrode. A Keithley power source was used to apply current. Data was collected on a Tandy computer.

Figure 6:
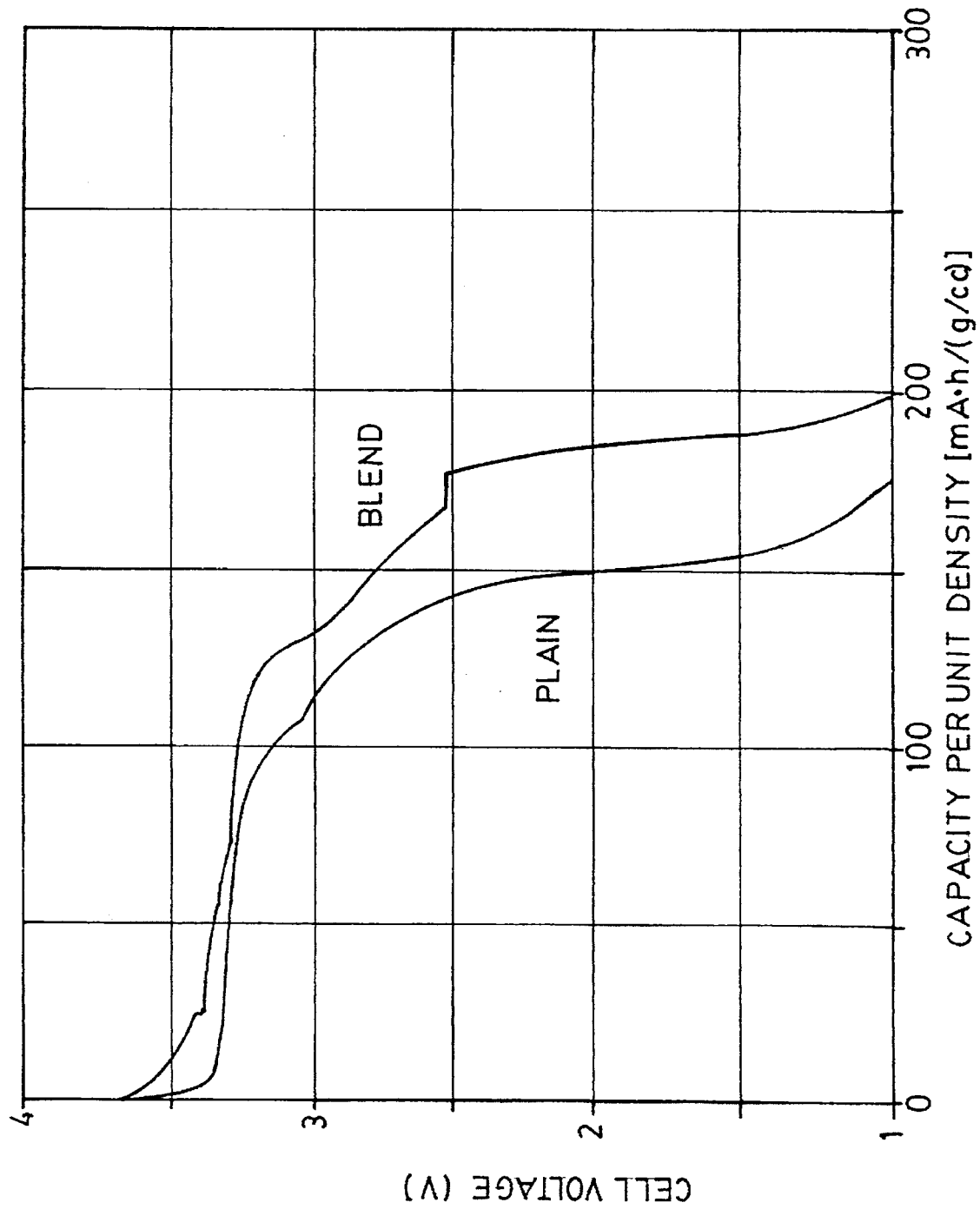
FIG. 6 is a graph showing plots of cell voltage versus capacity per unit density for a blend of 50 wt % of the carbon complex (made from a carbon black substrate) and 50 wt % plain carbon black, identified as the "blend" plot, and for plain carbon black alone, identified as the "plain" plot.

To maintain good electrode pore size and distribution, and yet assess the effect of increased electrode conductivity, discharge testing of acetylene carbon black electrodes employed electrodes made from plain carbon black alone and blended with the carbon complex of the present invention having carbon filaments grown on a carbon black substrate. In the blend, the plain carbon black provided retention of good pore size and distribution, while the carbon complex helped the connectivity. FIG. 6 compares the discharge performance of plain carbon black, identified as the "plain" plot, having a density of 0.39 g/cm$^3$ (not pressed), with that of a blend of 50 wt. % carbon complex (with carbon filaments grown on carbon black) and 50 wt. % plain carbon black, identified as the "blend" plot, having a density of 0.29 gm/cm$^3$ (not pressed). Since the experiment was conducted at a constant current of 3 mA, the capacity (in units of mA·h) is directly proportional to the time of discharge. In other words, the horizontal axis is related to the lifetime of the cell during constant current discharge. The electrodes for both cases were prepared identically, except for the difference in material. An improvement of approximately 40 mA·h per unit density was achieved when discharged to 2 volts.

Figure 7:
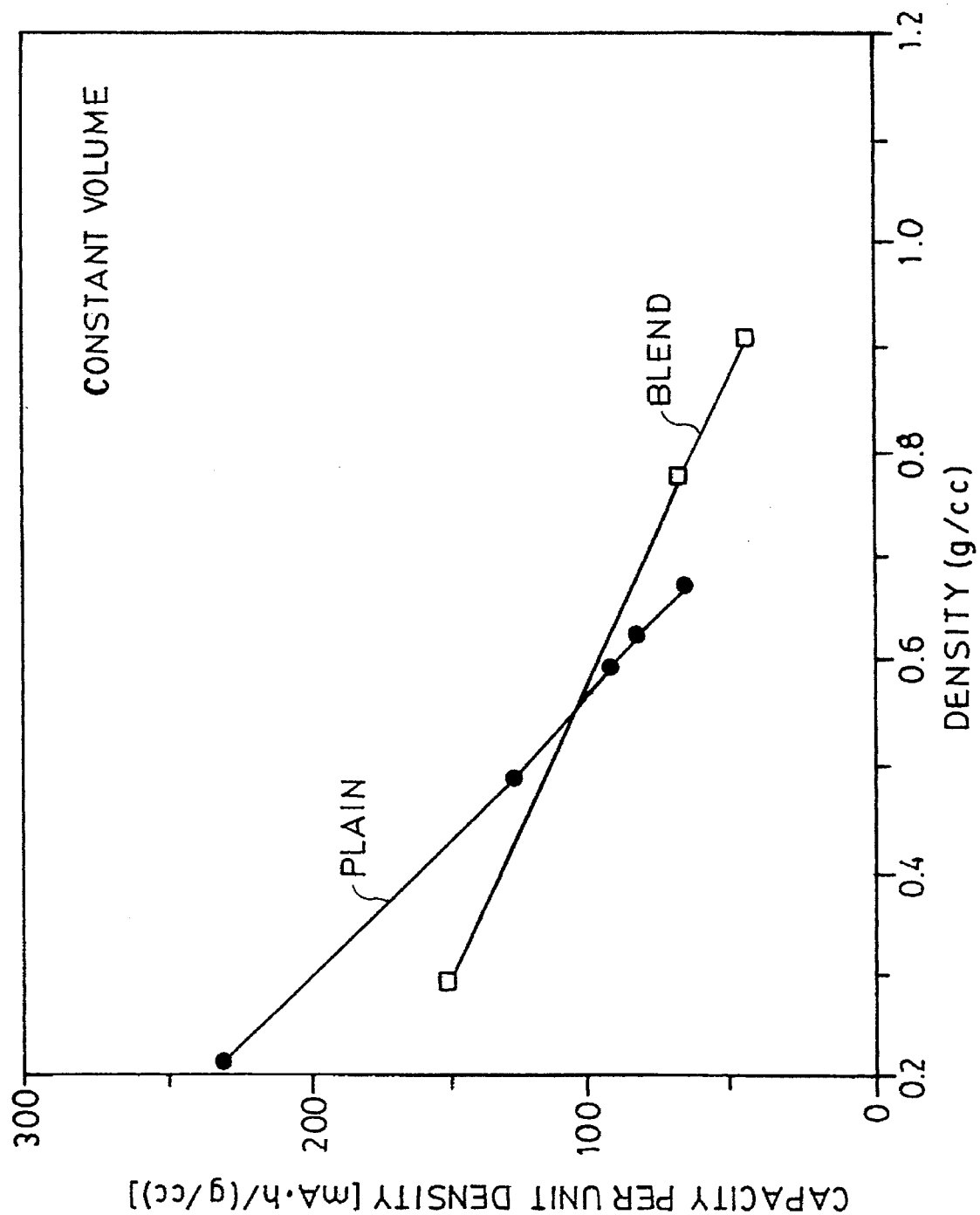
FIG. 7 is a graph showing capacity per unit density versus density plots for both a blend of 50 wt % of the carbon complex of the present invention (made from a carbon black substrate) and 50 wt % plain carbon black, identified as the "blend" plot, and plain carbon black alone, identified as the "plain" plot.

With a carbon reduction electrode of fixed volume, the cell capacity decreased with increasing density of the carbon reduction electrode, such that the plot of the capacity per unit density versus the density was a straight line of negative slope. This is due to the filling of pores in the reduction electrode by the reduction reaction product. FIG. 7 shows plots for plain acetylene carbon black, identified as the "plain" plot, and a blend of 50 wt. % carbon complex (with carbon filaments grown on carbon black) and 50 wt. % plain carbon black, identified as the "blend" plot. The plot for plain carbon black had a more negative slope, such that the blend gave a higher capacity per unit density than the plain carbon black at densities above 0.55 g/cm$^3$. The different densities were obtained by compression of the carbon particles at different pressures. To attain the same density, the plain carbon black required a much higher pressure than the blend. This is due to the resilient nature of carbon black compact. Thus, the electrode with the blend is easier to fabricate than that with plain carbon black, if a high density is desired. A high density corresponds to a greater energy density which is a desirable property in batteries.

Example 5

The adhesion of the carbon filaments to the acetylene carbon black in the carbon complex was tested by shaking about 0.5 cm$^3$ of the complex in ethanol contained in a 10 ml beaker, which was placed in water in an ultrasonic cleaner for 15 minutes. Subsequent scanning electron microscope examination revealed no sign of filaments coming off.

Although the invention has been described in detail for the purpose of illustration, it is understood that such detail is made solely for that purpose and variations can be made therein by those skilled in the art without departing from the spirit and scope of the invention which is defined by the following claims.

What is claimed:

1. A particulate carbon complex comprising:
   a carbon black substrate and
   a plurality of carbon filaments each having a first end attached to said carbon black substrate and a second end distal from said carbon black substrate, wherein said particulate carbon complex transfers electrical current at a density of 7000 to 8000 mA/cm$^2$ for a $Fe^{+2}/Fe^{+3}$ oxidation/reduction electrochemical reaction couple carried out in an aqueous electrolyte solution containing 6 mM potassium ferrocyanide and 1M aqueous potassium nitrate.

2. A particulate carbon complex according to claim 1, wherein said carbon black substrate has pores less than 5000 Angstroms in diameter.

3. A particulate carbon complex according to claim 1, wherein said plurality of carbon filaments each have a diameter of less than 5000 Angstroms.

4. A particulate carbon complex according to claim 1, wherein said plurality of carbon filaments are activated.

5. A particulate carbon complex according to claim 1 further comprising:

a particulate metal catalyst material at the second end of each carbon filament, wherein the metal in said particulate metal catalyst material is selected form the group consisting of iron, nickel, cobalt, zinc, platinum, and mixtures thereof.

6. A particulate carbon complex according to claim 5, wherein said particulate metal catalyst has a diameter of less than 5000 Angstroms.

7. A particulate carbon complex according to claim 1, wherein said plurality of carbon filaments each comprise a hollow core surrounded by an outer substantially continuous layer of carbon atoms.

8. A composite comprising:

a particulate carbon complex according to claim 1 and a dissimilar material in admixture with said particulate carbon complex, wherein said dissimilar material is selected from the group consisting of metal, ceramic, glass, polymer, and mixtures thereof.

9. A composite according to claim 8, wherein said carbon complex lowers the coefficient of thermal expansion of said composite.

10. A composite according to claim 8, wherein said carbon complex enhances electrical and thermal conductivity.

11. A particulate carbon complex according to claim 1, wherein the carbon black substrate is acetylene black.

12. A composite according to claim 8, wherein the carbon black substrate is acetylene black.

* * * * *